(12) United States Patent
Schaffner et al.

(10) Patent No.: US 7,098,198 B2
(45) Date of Patent: *Aug. 29, 2006

(54) COMPOSITIONS OF EZETIMIBE AND METHODS FOR THE TREATMENT OF CHOLESTEROL-ASSOCIATED BENIGN AND MALIGNANT TUMORS

(75) Inventors: Carl P. Schaffner, Hamilton, NJ (US); Keith R. Solomon, Boston, MA (US)

(73) Assignee: Karykion, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/128,140

(22) Filed: May 12, 2005

(65) Prior Publication Data

US 2005/0209167 A1    Sep. 22, 2005

Related U.S. Application Data

(62) Division of application No. 10/630,578, filed on Jul. 30, 2003, now Pat. No. 6,933,292.

(60) Provisional application No. 60/399,690, filed on Jul. 30, 2002.

(51) Int. Cl.
*A61K 31/56* (2006.01)
*A61K 31/33* (2006.01)
*A61K 31/397* (2006.01)
*A61K 31/445* (2006.01)
*A61K 31/40* (2006.01)

(52) U.S. Cl. ............. 514/171; 514/183; 514/210.02; 514/324; 514/414; 514/618; 514/645; 514/651

(58) Field of Classification Search ............ None
See application file for complete search history.

(56) References Cited

U.S. PATENT DOCUMENTS 6,534,540 B1 * 3/2003 Kindness et al. ............ 514/461

2001/0041713 A1 * 11/2001 Waldstreicher et al. ..... 514/284

FOREIGN PATENT DOCUMENTS

| WO | WO 93/02048 | * | 2/1993 |
| WO | WO 94/17038 | * | 8/1994 |
| WO | WO 95/08532 | * | 3/1995 |

OTHER PUBLICATIONS

Webster's II New Riverside University Dictionary, published 1984, see pp. 933 and 1208.*
Hawk et al., Primary Cancer Prevention Trails, Hematology/Oncology Clinics of North America, vol. 14, No. 4, Aug. 2000, pp. 809-830.*

* cited by examiner

*Primary Examiner*—Raymond J. Henley, III
(74) *Attorney, Agent, or Firm*—Fox Rothschild LLP

(57) ABSTRACT

A method of prevention or treatment of a cholesterol-associated tumor is provided which comprises administering a therapeutically effective amount of an azetidinone-based cholesterol absorption inhibitor, preferably ezetimibe (SCH 58235) and/or its phenolic glucuronide, or at least one ezetimibe analog, e.g., SCH 48461 and SCH 58053, to a patient wherein the patient is either at risk of developing a cholesterol-associated tumor or already exhibits a cholesterol-associated tumor. Formulations of ezetimibe are also provided for the prevention or treatment of a cholesterol-associated tumor further comprising at least one other anti-cancer agent. An article of manufacture is also provided which comprises a container, instructions, and a composition, wherein the composition comprises a therapeutically effective amount of an azetidinone-based cholesterol absorption inhibitor, preferably ezetimibe or its phenolic glucuronide, and the instructions are for the administration of the composition for the prevention or treatment of a cholesterol-associated tumor.

20 Claims, No Drawings

COMPOSITIONS OF EZETIMIBE AND METHODS FOR THE TREATMENT OF CHOLESTEROL-ASSOCIATED BENIGN AND MALIGNANT TUMORS

Priority is derived herein from U.S. application Ser. No. 10/630,578, filed Jul. 30, 2003, now U.S. Pat. No. 6,933, 292, and from U.S. Provisional application Ser. No. 60/399, 690, filed Jul. 30, 2002.

FIELD OF THE INVENTION

The invention relates to the prevention and/or treatment of cholesterol-associated tumors by means of administering azetidinone-based cholesterol absorption inhibitors. Particularly, hypertrophy of prostate tissues, breast tissues, endometrial tissues, and colon tissues are controlled by the oral administration of a therapeutically effective amount of ezetimibe, for example, or its phenolic glucuronide. Combinations of ezetimibe, and/or at least one of its analogs efficacious in controlling the absorption of cholesterol, and at least one other anticancer agent selected from the group consisting of (a steroidal antiandrogen, a non steroidal antiandrogen, an estrogen, diethylstilbestrol, a conjugated estrogen, a selective estrogen receptor modulator (SERM), a taxane, and a LHRH analog) are provided for the prevention or treatment of cholesterol-associated tumors.

BACKGROUND OF THE INVENTION

Although cholesterol metabolism has been studied extensively in the liver and intestinal tract of humans and experimental animals little attention has been directed to the cholesterol metabolism in the male prostate gland and the female mammary gland in both their normal and pathologic diseased states. The etiology and progression for benign and malignant tumors of these glands still remains largely a mystery. Cholesterol-rich diets have had a significant epidemiological association with the variety of human cancer diseases. Particularly, cancers of the prostate and mammary glands and of the colon have been linked to high-fat "western" diets including the intake of fat of animal origin. Kolonel, et al., 1999, *J. Natl. Cancer Inst.,* 91:414–428; Willett, 1989, *Nature,* 338:389–394. The mechanisms, however, by which these cancers are initiated and progress, as related to the dietary fat, are poorly understood.

The polyene macrolides and in particular, the aromatic heptaene macrolide, candicidin, have been in clinical use for the treatment of human benign prostatic hyperplasia for many years in several countries. Various other hypocholesterolemic drugs that interfere with cholesterol absorption and resorption in the gastrointestinal tract have also been in clinical use for the same human prostatic disease. Schaffner, 1983, in: *"Benign Prostatic Hypertrophy"*, Frank Hinman, Jr. ed. Springer-Velag, New York, pp. 280–307 reviewed clinical studies with candicidin and other polyene macrolides. Candicidin in long-term rat studies has been shown to inhibit tumor initiation and progression as compared to untreated controls. Haditirto, 1974, Ph.D. Dissertation, Rutgers University. Other inhibitors of cholesterol absorption—resorption include the bile acid sequestering anionic exchange resins such as Cholestyramine® and Colestipol®. These have also been shown to alter the course of prostatic disease in animals and humans. Colestipol® inhibited benign prostatic hypertrophy in hamsters. Wang. et al., 1976, Investigative Urol. 14:66–71. Cholestyramine® has been shown to be effective in some patients with prostatic carcinoma. Addleman, 1972, N. England J. Med., 287:1047. As hypocholesterolemic drugs, the phytosterols, beta-sitosterol and stigmasterol, for example, are also known for their ability to inhibit cholesterol absorption and resorption by a mass action effect requiring large doses. In a controlled double blind study beta-sitosterol was found to be effective in the treatment of benign prostatic hyperplasia. Ebbinghaus et al., 1977, *Z. Allg. Med.,* 53:1054–1058. It has been approved for human use in Europe. The phytosterols are also components of a variety of herbal medicines prescribed for the treatment of prostate disease. Extracts of the berries of the plant, saw palmetto, and the bark of *Pygeum africanum,* also known as Tadenan, for example, contain significant quantities of beta-sitosterol.

SUMMARY OF THE INVENTION

The present invention is directed to methods of prevention or treatment of a cholesterol-associated tumor comprising administering a therapeutically effective amount of an azetidinone-based cholesterol absorption inhibitor particularly ezetimibe, one of its analogs or its phenolic glucuronide to a patient wherein the patient is either at risk of developing a cholesterol-associated tumor or already exhibits a cholesterol-associated tumor.

In addition, the current invention is directed to methods of using ezetimibe to prevent or treat a cholesterol-associated tumor selected from the group consisting of either benign or malignant tumors of the prostate, breast, endometrium and colon.

The invention is further directed to methods and compositions for co-administering ezetimibe and at least one other anticancer agent selected from the group consisting of a steroidal antiandrogen, a non-steroidal antiandrogen, an estrogen, diethylstilbestrol, a conjugated estrogen, a selective estrogen receptor modulator (SERM), a taxane, and a LHRH analog for the prevention or treatment of a cholesterol-associated tumor.

Further the invention is directed to an article of manufacture comprising indication labeling; particularly, an article of manufacture comprising a container, instructions, and a composition, wherein the composition comprises a therapeutically effective amount of an azetidinone-based cholesterol absorption inhibitor, preferably ezetimibe, and the instructions are for the administration of the composition for the prevention or treatment of a cholesterol-associated tumor.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Cholesterol Mediation of Disease Conditions

The epoxycholesterols, for example, have long been attributed to have mitogenic, mutagenic, carcinogenic and cyotoxic properties. The in vivo level of epoxycholesterols as oxidized metabolites of cholesterol in the male prostate and female mammary gland, for example, is the direct result of cholesterol content. Particularly, cholesterol and its metabolites including cholesterol epoxides (epoxycholesterols), e.g., cholesterol 5β and 6β-epoxide, are related to and mediate disease processes, particularly benign and/or malignant cholesterol-associated tumors or otherwise cholesterol-associated abnormal or cancerous cell growth or cell-mass including but not limited to tumors associated with prostate, breast, endometrial, and colon tissues. In these tissues the epoxycholesterols also serve as a marker of benign and malignant diseases.

Prostate

The cholesterol content of the human prostate gland tissues, for example, doubles with the appearance of prostate tumors. Swyer, 1942, Cancer Res., 2:372–375; Schaffner, C. P., et al., Cancer Detect. Prevent., 1980, vol. 3, p 143. Further, the appearance of the cholesterol epoxides has been reported in the tissues and secretions of diseased human prostate glands confirming the doubling of tissue cholesterol content and the significant content of the epoxycholesterols with the diagnosis of human prostatic hyperplasia and carcinoma. Sporer et al., 1982, Urology, 6:244–250.

Breast and Endometrial

Studies with the human female mammary gland also report significant increases of cholesterol in the breast fluid aspirates and the simultaneous appearance of the epoxycholesterols, for example, with the aging female human mammary gland. Particularly, the appearance of isometric epoxycholesterols, e.g., beta-epoxycholesterol, is correlated to benign and malignant breast tumors. Petrakis, et al., 1981, Cancer Res., 41:2563–2565; Wrench et al., 1989, Cancer Res., 49:2168–2174. Elevated beta-epoxycholesterol is also detected, for example, in the plasma of endometrial cancer patients. Kucuk, et al., 1994, Can Epidemiol. Biomark. Prevention, 3:57 1–574. The appearance of the epoxycholesterols, e.g., beta-epoxycholesterol, is directly related to the increase of cholesterol in body fluids and tissues.

Azetidinone-Based Cholesterol Absorption Inhibitors

The present invention is directed toward compositions of azetidinone-based cholesterol absorption inhibitors, e.g., ezetimibe and its glucuronides and its analogs, for the reduction of cholesterol levels in vivo and reduces epoxycholesterol formation and the initiation and progression of benign and malignant tumors and methods of use therefore. The compositions and methods of the invention are particularly for the prevention or control or treatment of benign or malignant cholesterol-associated tumors or cholesterol-associated cell growth or cell-masses including but not limited to tumors associated with prostate, colon, endometrial, or breast tissues—or—prostate, colon, breast, or endometrial cancer. Methods are provided for the prevention and treatment of cholesterol-associated tumors by the inhibition of their initiation and progression by the inhibition of cholesterol absorption and resorption in the gastrointestinal tract. Oral administration of ezetimibe compositions disclosed herein, for example, are preferred embodiments of the present invention for the treatment and/or prevention of benign prostatic hypertrophy or other cholesterol-related benign or malignant tumors, for example, associated with prostate, breast, endometrial or colon tissues.

Ezetimibe by the oral route, for example, has a significant effect on the initiation and progression of prostatic disease and other cholesterol-associated tumors, for example, in experimental animals. The BIO 87.20 male Syrian hamster is a well-known inbred line that develops, spontaneously, an age-dependent and genetic related cystic prostatic hypertrophy and is recognized in the art as an excellent model for human prostate disease. See, Examples I–III, infra. Ezetimibe by the oral route inhibits the development of cystic prostatic hypertrophy in the BIO 87.20 male Syrian hamster. Ezetimibe also inhibits other cholesterol-associated tumor formation in this animal disease model. Treatment of BIO 87.20 male Syrian hamsters with ezetimibe, beginning at 6 months of age, inhibits prostatic enlargement. BIO 87.20 male Syrian hamsters treated with ezetimibe, beginning at 12 months of age (when the prostatic enlargement is already in progress), reduces the prostatic mass or volume. Higher doses of ezetimibe, for example, at the 1000 µg/kg body weight have a greater effect on the inhibition and reversal of the prostate enlargement of the BIO 87.20 hamster. Further, histopathological examination of the prostates, for example, of the ezetimibe treated BIO 87.20 hamsters show a more normal histology, as seen in prostate sections of the BIO 1.5 hamsters. The BIO 87.20 male Syrian hamster is noted for the emergence of tumors throughout the body at 18 months of age or older. At 18 months the BIO 87.20 hamsters demonstrate the presence of cholesterol-associated tumors in addition to that of the prostate gland. The BIO 87.20 control animals of Example II herein, for example, exhibit several different tumors at the end of the experiment; whereas, the BIO 87.20 ezetimibe-treated animals of the same age exhibit no tumors.

Prostate cancer is a leading cause of mortality in males in North America with between 30,000 to 40,000 deaths per year in the United States. While chemotherapy has not been very efficacious in the treatment of prostate cancer, an alternative approach has been to target prostate cancer cell survival pathways, particularly the PI3 kinase/Akt/PTEN signaling axis, which has been identified as an important cell survival mechanism in PCa and other cancers. Recently it has been determined that membrane cholesterol is an important component of a mechanism that transfers survival signals from the cell exterior to the Akt1 serine-threonine kinase. It has also been shown recently that elevated serum cholesterol accelerates the growth, lowers the extent of cellular apotosis, and increases the level of Akt activation in prostate tumors within a murine prostate cancer model. Findings indicate that cholesterol plays a critical role in the ability of prostate cancer cells to resist apoptotic stimuli. The role of cholesterol in prostate cancer cell survival is so critical that drugs that bind cholesterol (polyene macrolides), extract cholesterol from membranes (cyclodextrin) or block cholesterol synthesis (statins) all alter essential membranes (lipid rafts) and reduce their capacity to regulate cell signaling. Cholesterol plays a crucial role in specifically regulating prostate cancer growth and survival. In these studies a unique prostate murine model system is used. This model features the human prostate adenocarcinoma cell line, LNCaP transfected with HB-EGF. LNCaP cells resemble typical prostate tumor cells in their general morphology, production of PSA and PTEN null status. Stable transfection with HB-EGF, a physiologically relevant EGFR ligand that originates in the prostatic stroma, permits LNCaP cells to form tumors in vivo in an androgen-independent manner. Subcutaneous implantation of these LNCaP cells into 4 quadrants of SCID mice results in rapid tumor growth in intact and castrated mice over an eight week period. Ezetimibe and related compounds SCH 48461 and SCH 58053 do not generally affect serum cholesterol levels in mice fed a low cholesterol diet, but do lower elevated serum cholesterol levels induced by high cholesterol diets. Mice placed on a high cholesterol diet 4 weeks prior to tumor implantation are started on ezetimibe and SCH 48461 @ 30 mg/kg of body weight 2 weeks after tumor implantation. After 12 weeks the evaluation of tumor volumes in each mouse as compared to the untreated controls revealed that drug treatment significantly inhibits the progression and growth of the implanted tumors.

Cholesterol-associated tumor as used herein refers to benign or malignant tumors or otherwise cholesterol-associated abnormal or cancerous cell growth or cell-mass including but not limited to tumors associated with prostate (for example, prostatic hyperplasia) tissue, colon tissue, breast tissue, or endometrial tissue—or—prostate cancer, colon cancer, breast cancer, or endometrial cancer.

Azetidinone-based cholesterol absorption inhibitors, for example, are described by Rosenblum, S. B., et al., J. Med. Chem., 41(6):973–80 (1998)). Azetidinone-based compounds are potent, orally active inhibitors of cholesterol absorption. Bioorg. Med. Chem., 7(10):2199–202 (1999). A particularly preferred azetidinone-based compound for use in compositions and methods of the present invention is ezetimibe (1-(4-fluorophenyl)-(3R)-[3-(4-fluorophenyl)-(3S)-hydroxypropyl]-(4S)-(4-hydroxyphenyl)-2-azetidinone) (also referred to in the literature as SCH 58235 or ZETIA®) and its phenolic glucuronide, SCH60663. Br. J. Pharmacol., 129(8):1748–54 (2000). Two other ezetimibe related analogs and cholesterol absorption inhibitors for use in compositions and methods of the present invention, for example, are referred to in the literature as: 1) SCH 58053 or (+)-7-(4-chlorophenyl)-2-(4-flourophenyl)-7-hydroxy-3R-(4-hydroxyphenyl)-2-azaspiro[3,5]nonan-1-one) J. Lipid Res., 43:1864–1873(2002) and 2) SCH 48461 or (3R)-3Phenylpropyl]-1,(4S)-bis(4-methoxyphenyl)-2-azetidinone. J Med. Chem., 41:973–980 (1998)

Ezetimibe's mode of action involves the inhibition of cholesterol absorption and resorption in the intestinal tract. This mechanism of action also involves the increased excretions of cholesterol and its intestinal generated metabolites with the feces. This effect of ezetimibe results in lowered body cholesterol levels, increased cholesterol synthesis, and decreased triglyceride synthesis. The increased cholesterol synthesis initially provides for the maintenance of cholesterol levels in the circulation, levels that eventually decline as the inhibition of cholesterol absorption and resorption continues. The overall effect of drug action is the lowering of cholesterol levels in the circulation and tissues of the body.

A preferred azetidinone-based cholesterol absorption inhibitors for use in compositions and methods of the present invention is ezetimibe or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

Another preferred azetidinone-based cholesterol absorption inhibitors is the phenolic glucuronide of ezetimibe (Br. J. Pharmacol., 129(8): 1748–54 (2000)) or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

The expression "prodrug" as used herein refers to compounds that are drug precursors which following administration, release the drug in vivo via chemical or physiological process (e.g., a prodrug on being brought to the physiological pH is converted to the desired drug form). Exemplary prodrugs upon cleavage release the corresponding free acid. For example, by means of hydrolyzable ester-forming residues of the compounds.

Compositions of the invention basically comprise an effective dose or a pharmaceutically effective amount or a therapeutically effective amount of an azetidinone based cholesterol absorption inhibitor, preferably ezetimibe and/or its phenolic glucuronide or at least one ezetimibe pharmacologically active analog, to prevent, or control the growth, or reduce the size of benign prostatic hypertrophy or other cholesterol-related benign or malignant tumors, for example, associated with prostate, breast, endometrial or colon tissues.

Compositions described herein comprise azetidinone-based cholesterol absorption inhibitors, preferably ezetimibe its phenolic glucuronide, or one of its analogs and may further comprise at least one other anticancer agent. These compositions are preferably orally administered. Solid dosage forms for oral administration include capsules, tablets, pills, powders and granules and for companion animals the solid dosage forms include an admixture with food and chewable forms. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings. In the case of chewable forms, the dosage form may comprise flavoring agents and perfuming agents.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between about 100 µg to about 200 µg/kg of body weight daily are administered to humans and other animals, e.g., mammals, to obtain effective release of ezetimibe for methods described herein.

Oral administration of ezetimibe, for example, inhibits both dietary and biliary cholesterol absorption and resorption in the intestinal tract, thereby lowering serum cholesterol levels as associated with the reduced low density lipoprotein (LDL) levels and increased high density lipoprotein (HDL) levels. The preferred dosage range of ezetimibe in compositions for administration to a patient in need of prevention or treatment described herein is from about 5 mg to about 150 mg per day. A more preferred range is from about 5 mg to about 100 mg per day. An even more preferred range is from about 8 mg to about 50 mg per day. A most preferred range is from about 10 mg to about 25 mg per day. A composition for oral administration which comprises about 10 mg ezetimibe for a single daily dosage to prevent, or control the growth, or reduce the size of benign prostatic hypertrophy or other cholesterol-related benign or malignant tumors, for example, associated with prostate, breast, endometrial or colon tissues, is a particularly preferred embodiment of the present invention. A composition for oral administration which comprises about 15 mg ezetimibe for a single daily dosage to prevent, or control the growth, or reduce the size of benign prostatic hypertrophy or other cholesterol-related benign or malignant tumors, for example, associated with prostate, breast, endometrial or colon tissues is another preferred embodiment of the present invention. A composition for oral administration which comprises about 20 mg ezetimibe for a single daily dosage to prevent, or control the growth, or reduce the size of benign prostatic hypertrophy or other cholesterol-related benign or malignant tumors, for example, associated with prostate, breast, endometrial or colon tissues is another preferred embodiment of the present invention. A composition for oral administration which comprises about 25 mg ezetimibe for a single daily dosage to prevent, or control the growth, or reduce the size of benign prostatic hypertrophy or other cholesterol-related benign or malignant tumors, for example, associated with prostate, breast, endometrial or colon tissues is another preferred embodiment of the present invention. A composition for oral administration which comprises about 30 mg ezetimibe for a single daily dosage to prevent, or control the growth, or reduce the size of benign prostatic hypertrophy or other cholesterol-related benign or malignant tumors, for example, associated with prostate, breast, endometrial or colon tissues is another preferred embodiment of the present invention. A composition for oral administration which comprises about 35 mg ezetimibe for a single daily dosage to prevent, or control the growth, or reduce the size of benign prostatic hypertrophy or other cholesterol-related benign or malignant tumors, for example, associated with prostate, breast, endometrial or colon tissues is another preferred embodiment of the present invention. A composition for oral administration which comprises about 40 mg ezetimibe for a single daily dosage to prevent, or control the growth, or reduce the size of benign prostatic hypertrophy or other cholesterol-related benign or malignant tumors, for example, associated with prostate, breast, endometrial or colon tissues—is another preferred embodiment of the present invention. A composition for oral administration which comprises about 45 mg ezetimibe for a single daily dosage to prevent, or control the growth, or reduce the size of benign prostatic hypertrophy or other cholesterol-related benign or malignant tumors, for example, associated with prostate, breast, endometrial or colon tissues—is another preferred embodiment of the present invention.

These compounds can be administered by any means known in the art. Such modes include oral, rectal, nasal, topical (including buccal and sublingual) or parenteral (including subcutaneous, intramuscular, intravenous and intradermal) administration.

For ease to the patient oral administration is preferred. However, as practiced by those skilled in the art other routes of administration may be necessary. Thus, depending upon the situation—the skilled artisan must determine which form of administration is best in a particular case—balancing dose needed versus the number of times per month administration is necessary.

Combination Therapy

Compositions of the invention comprise an effective dose or a pharmaceutically effective amount or a therapeutically effective amount of an azetidinone-based cholesterol absorption inhibitor, preferably ezetimibe or its phenolic glucuronide, and at least one other anticancer agent, for the treatment or prevention of benign prostatic hypertrophy or other cholesterol-related benign or malignant tumors, for example, associated with prostate, breast, endometrial or colon tissues. Examples of agents for use in compositions and methods of the invention described herein include but are not limited to steroidal or non steroidal antiandrogens (e.g., finasteride (PROSCAR®), cyproterone acetate (CPA), flutamide (4'-nitro-3'-trifluorormethyl isobutyranilide), bicalutamide (CASODEX®), and nilutamide), estrogens, diethylstilbestrol (DES), conjugated estrogens (e.g., PREMARIN®), selective estrogen receptor modulator (SERM) compounds (e.g., tamoxifen, raloxifene, droloxifene, idoxifene), Taxanes (e.g., paclitaxel (TAXOL®), docetaxel (TAXOTERE®)), LHRII analogs (e.g., goserelin acetate (ZOLADEX®), leuprolide acetate (LUPRON®)).

Taxanes

Docetaxel (TAXOTERE®) based regimens, for example, are reported to be treatment options for the management of patients with advanced, androgen-independent prostate cancer. Docetaxel in combination with ezetimibe, for example, should achieve a significant response in treatment or prevention of benign prostatic hypertrophy or other cholesterol-related benign or malignant tumors, for example, associated with prostate, breast, endometrial or colon tissues in patients with measurable disease. See, e.g., Oncology (Huntingt.), 16(6 Suppl. 6):63–72 (2002). Any taxane may be used as an anticancer agent for use in the compositions and methods of this invention.

A preferred method of the invention accordingly comprises orally co-administering to a patient in need of treatment a therapeutically effective amount of an azetidinone-based cholesterol absorption inhibitor, preferably ezetimibe, and a taxane preferably selected from the group consisting essentially of (paclitaxel and docetaxel) or an effective derivative or analog thereof for the treatment or prevention of benign prostatic hypertrophy or other cholesterol-related benign or malignant tumors, for example, associated with prostate, breast, endometrial or colon tissues. See, e.g., U.S. Pat. No. 6,395,770 Method and compositions for administering taxanes orally to human patients, May 28, 2002; U.S. Pat. No. 6,380,405 Taxane Prodrugs, Apr. 30, 2002; U.S. Pat. No. 6,239,167 Antitumor compositions containing taxane derivatives, May 29, 2001.

SERMs

An azetidinone-based cholesterol absorption inhibitor, preferably ezetimibe, may be combined with a mammalian selective estrogen receptor modulator (SERM) to prevent, or control the growth, or reduce the size of benign pro static hypertrophy or other cholesterol-related benign or malignant tumors, for example, associated with prostate, breast, endometrial or colon tissues. Any SERM may be used as an anticancer agent for use in the compositions and methods of this invention. The term selective estrogen receptor modulator includes both estrogen agonist and estrogen antagonists and refers to compounds that bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. A preferred SERM is tamoxifen: (ethanamine,2-[-4-(1,2-diphenyl-1-butenyl)phenoxy]-N,N-dimethyl, (Z)-2,2-hydroxy-1,2,3-propanetri-carboxylate (1:1)) and associated compounds which are disclosed in U.S. Pat. No. 4,536,516, the disclosure of which is hereby incorporated by reference. Another related compound is 4-hydroxy tamoxifen which is disclosed in U.S. Pat. No. 4,623,660, the disclosure of which is hereby incorporated by reference. Another preferred SERM is raloxifene: (methanone, [6-hydroxy-2-(4-hydroxyphenyl)benzo[b]thien-3-yl][4-[2-(1-piperidinyl)ethoxy]phenyl]-, hydrochloride) and associated compounds which are disclosed in U.S. Pat. No. 4,418,068, the disclosure of which is hereby incorporated by reference. Another preferred SERM is idoxifene: Pyrrolidine, 1-1-[4-[-1-(4-iodophenyi)-2-phenyl-1-Butenyl] phenoxy]ethyl] and associated compounds which are disclosed in U.S. Pat. No. 4,839,155, the disclosure of which is hereby incorporated by reference.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day. In particular, an effective dosage for tamoxifen is in the range of 0.1 to 100 mg/kg/day, preferably 0.1 to 5 mg/kg/day. In particular, an effective dosage for 4-hydroxy tamoxifen is in the range of 0.0001 to 100 mg/kg/day, preferably 0.001 to 10 mg/kg/day.

A preferred method of the invention accordingly comprises orally co-administering to a patient in need of treatment a therapeutically effective amount of an azetidinone-based cholesterol absorption inhibitor, preferably ezetimibe, and a SERM selected from the group consisting essentially of (tamoxifen, raloxifene, droloxifene, and idoxifene) or an effective derivative or analog thereof for the treatment or prevention of benign prostatic hypertrophy or other cholesterol-related benign or malignant tumors, for example, associated with prostate, breast, endometrial or colon tissues. See, e.g., U.S. Pat. No. 5,047,431, U.S. Pat. No. 6,245,352 and U.S. Pat. No. 5,972,383 the disclosures of which are hereby incorporated by reference.

Steroidal or Non Steroidal Antiandrogens

An azetidinone-based cholesterol absorption inhibitor, preferably ezetimibe, may be combined with a steroidal or non steroidal antiandrogen to prevent, or control the growth, or reduce the size of benign prostatic hypertrophy or other cholesterol-related benign or malignant tumors, for example, associated with prostate, breast, endometrial or colon tissues. Any steroidal or non-steroidal antiandrogen may be used as the second compound of this invention. See, e.g., U.S. Pat. No. 5,610,150, and U.S. Pat. No. 6,015,806.

A preferred method of the invention accordingly comprises orally co-administering to a patient in need of treatment a therapeutically effective amount of an azetidinone-based cholesterol absorption inhibitor, preferably ezetimibe, and a steroidal or non steroidal antiandrogen selected from the group consisting essentially of (finasteride (PROSCAR®)), cyproterone acetate (CPA), flutamide(4'-nitro-3'-trifluorormethyl isobutyranilide), bicalutamide (CASODEX®), and nilutamide) or an effective derivative or analog thereof for the treatment or prevention of benign pro static hypertrophy or other cholesterol-related benign or malignant tumors, for example, associated with prostate, breast, endometrial or colon tissues.

Finasteride (PROSCAR®), in an amount of between about 1 mg to about 10 mg, preferably about 5 mg, may be orally co-administered in a pharmaceutical composition which further comprises about 10 mg ezetimibe, for example, for a single daily dosage, to prevent or control the growth, or reduce the size of benign prostatic hypertrophy or other cholesterol related benign or malignant tumors, for example, associated with prostate.

Luteinizing Hormone Releasing Hormone (LHRH) Analog or Agonist

An azetidinone-based cholesterol absorption inhibitor, preferably ezetimibe, may be co-administered with a luteinizing hormone releasing hormone (LHRH) analog or agonist to prevent, or control the growth, or reduce the size of benign prostatic hypertrophy or other cholesterol-related benign or malignant tumors, for example, associated with prostate, breast, endometrial or colon tissues. Any LHRH analog or agonist may be used as the second compound of this invention.

A preferred method of the invention accordingly comprises orally co-administering to a patient in need of treatment a therapeutically effective amount of an azetidinone-based cholesterol absorption inhibitor, preferably ezetimibe, and a LHRH analog or agonist selected from the group consisting essentially of (goserelin acetate (ZOLADEX®) and leuprolide acetate (LUPRON®)) or an effective derivative or analog thereof for the treatment or prevention of benign prostatic hypertrophy or other cholesterol-related benign or malignant tumors, for example, associated with prostate, breast, endometrial or colon tissues.

Estrogens, Diethylstilbestrol (DES), Conjugated Estrogens (e.g., PREMARIN®)

An azetidinone-based cholesterol absorption inhibitor, preferably ezetimibe, may be co-administered with an estrogen, diethylstilbestrol (DES), or conjugated estrogen to prevent, or control the growth, or reduce the size of benign prostatic hypertrophy or other cholesterol-related benign or malignant tumors, for example, associated with prostate, breast, endometrial or colon tissues.

A preferred method of the invention accordingly comprises orally co-administering to a patient in need of treatment a therapeutically effective amount of an azetidinone-based cholesterol absorption inhibitor, preferably ezetimibe, and a estrogen, diethyistilbestrol (DES), or conjugated estrogen e.g., PREMARIN® or an effective derivative or analog thereof for the treatment or prevention of benign prostatic hypertrophy or other cholesterol-related benign or malignant tumors, for example, associated with prostate, breast, endometrial or colon tissues.

Article of Manufacture

An article of manufacture is provided which comprises a container, e.g., a vial, written instructions, and a formulated composition, wherein the composition comprises a therapeutically effective amount of an azetidinone-based cholesterol absorption inhibitor, and the instructions are for—or— indicate the administration of the composition for the prevention or treatment of a cholesterol-associated tumor, e.g., prostate tumor, breast tumor, endometrial tumor, and/or colon tumor. A preferred article of manufacture comprises ezetimibe as the azetidinone-based cholesterol absorption inhibitor. Another preferred article of manufacture so described further comprises at least one other anticancer agent, e.g., a steroidal antiandrogen, a non-steroidal antiandrogen, an estrogen, diethylstilbestrol, a conjugated estrogen, a selective estrogen receptor modulator (SERM), a taxane, and/or a LHRH analog.

EXAMPLES

Example I

Experimental Animal Groups

The BIO 87.20 male Syrian hamster is a well-known inbred line that develops, spontaneously, an age-dependent and genetic related cystic prostatic hypertrophy and is recognized in the art as an excellent model for human prostate disease. See, e.g., Homburger et al., 1970, Proc. Soc. Exptl. Biol. Med., 134:284–286; Homburger, 1972, Health Lab Sci., 9:103–111; Wang et al., 1976, Invest. Urol., 14:66–71. The BIO 87.20 strain of hamster develops multiple tumors after 12 months of age.

Histopathological examination of the enlarged prostate of the BIO 87.20 male Syrian hamster generally reveals a cystic dilation of the prostatic acini, which are filled with eosinophilic amorphous material. The stromal hyperplasia and changes in the epithelial cells are also observed upon microscopic examination. Control male Syrian hamster such as the BIO 1.5 strain do not generally develop tumors at 12 months or older. The BIO 87.20 and BIO 1.5 strains of male Syrian hamster are employed in the ezetimibe studies presented herein. BIO 87.20 hamsters maintained on a cholesterol-rich diet revealed on autopsy a marked accumulation of cholesterol in the liver and severe hypercholesterolemia that led to animal death. The study further clearly revealed that whereas hepatic cholesterol synthesis in the normal hamster is under negative feedback control with dietary cholesterol, hepatic cholesterol synthesis in the BIO 87.20 hamster is under no such feedback control. Schaffner et al., *Lipids* 16:835–840 (1981). The defect in cholesterol synthesis and the development of cystic prostatic hypertrophy in the BIO 87.20 male hamster is related.

16 BIO 1.5 and 48 BIO 87.20 male Syrian hamsters are obtained from Bio Breeders, Inc. Boston, Mass. Among these animals, 8 BIO 1.5 and 24 BIO 87.20 hamsters are 6 months of age, while the remainder, consisting of 6 BIO 1.5 and 24 BIO 87.20 hamsters, are 12 months of age. The animals are housed in individual cages. All animals are given water ad libitum and are housed under automatic regime of 12 hours artificial light and 12 hours darkness. Food consumption is be monitored to ensure equivalent intake in all animals. The drug, ezetimibe, is powdered and mixed into ground PURINA® hamster chow. Concentrations of ezetimibe, in the food, is adjusted according to quantity of food intake per hamster per day and expressed as average μg of ezetimibe per kg body weight per day.

The animals are divided into 8 experimental groups containing 8 animals each. The groups may be characterized as follows:

| Group I | BIO 1.5 | Controls, 6 months of age |
|---|---|---|
| Group II | BIO 1.5 | Controls, 12 months of age |
| Group III | BIO 87.20 | Controls, 6 months of age |
| Group IV | BIO 87.20 | Controls, 12 months of age |
| Group V | BIO 87.20 | Treated, 6 months of age, ezetimibe @ 100 μg/kg body weight |
| Group VI | BIO 87.20 | Treated, 6 months of age, ezetimibe @ 1000 μg/kg body weight |
| Group VII | BIO 87.20 | Treated, 12 months of age, ezetimibe @ 100 μg/kg body weight |
| Group VIII | BIO 87.20 | Treated, 12 months of age, ezetimibe @ 1000 μg/kg body weight |

Control BIO 1.5 and control and treated BIO 87.20 male Syrian hamsters, both 6 and 12 months of age, are used as follows. In the treated group of BIO 87.20 male Syrian hamsters, ezetimibe is administered as a powder in the diet. Treatment with doses of ezetimibe of 100 and 1000 micrograms per kilogram body weight of the BIO 87.20 animals is continued for 6 months. Control BIO 1.5 and BIO 87.20 animals do not receive ezetimibe. The food consumption of all groups is monitored, in order to ensure comparable food intake. After 6 months of treatment the animals are sacrificed and the prostate glands excised, weighed and preserved for histopathological examination.

At the termination of the experiment, after 6 months, it is evident that all control BIO 87.20 hamsters have enlarged prostate glands. This is further evident when the ventral prostate glands are excised and weighed. By sharp contrast none of the BIO 1.5 hamsters, at 12 or 18 months of age show an enlargement of the prostate gland. In the BIO 87.20 control groups the enlargement of the gland is more pronounced at 18 months than at 12 months. The progression of prostatic enlargement is enhanced with time in this control group. Examination of the prepared sections of the BIO 87.20 hamsters, at 12 and 18 months of age, reveal histologically the cystic prostatic hypertrophy that is well-known for this hamster strain. Further, microscopic examination reveals a distended acinus, which is absent in the examination of BIO 1.5 hamster prostate sections.

Example II

Ezetimibe Treatment of BIO 87.20 Hamsters 6 Months of Age

Six months of ezetimibe treatment of the BIO 87.20 male Syrian hamsters, beginning at 6 months of age shows a marked inhibitory effect on the prostate gland volume as compared to the untreated control BIO 87.20 hamsters. The effect of 1000 μg ezetimibe/kg-body weight demonstrates a greater inhibitory effect on size increase of the prostate gland than with the drug ezetimibe/kg-body weight dose. Upon histopathological examination it is further evident that after 6 months of ezetimibe treatment a marked reduction in the cystic prostatic hypertrophy is seen in treated animals when compared to the untreated control BIO 87.20 animals. After 6 months of ezetimibe treatment the ventral prostate gland weights of the BIO 87.20 animals are similar to those of the BIO 1.5 (control) hamsters (where the development of cystic prostatic hypertrophy is not seen) of the same age.

Example III

Ezetimibe Treatment of BIO 87.20 Hamsters 12 Months of Age

Cystic prostatic hypertrophy is generally well established in BIO 87.20 male Syrian hamster at 12 months of age. All of the male Syrian hamsters, i.e., control and treated BIO 87.20, and control BIO 1.5 are 12 months old at the beginning of the experiment. Treatment of the BIO 87.20 animals with doses of ezetimibe of 100 and 1000 micrograms per kilogram body weight is continued for 6 months. After the treatment, the excised ventral prostate weights are markedly reduced as compared to untreated BIO 87.20 controls. Further, the level of effect is again significantly greater at the higher dosage of ezetimibe. These results therefore indicate that ezetimibe also reverses the prostatic enlargement once it has taken place.

Miscellaneous tumors other than that of the prostate gland are observed in the examination of the untreated BIO 87.20 control hamsters. By contrast, very few tumors are observed in the ezetimibe treated BIO 87.20 animals, which are administered an oral dose at 1000 μg/kg-body weight.

Example IV

Ezetimibe Treatment of SCID Mice Transplanted with LNCaP Cells Transfected with HB-EGF.

Subcutaneous implantations of LNCaP cells into 4 quadrants of SCID mice ($2 \times 10^6$ cells in 150 ul Matrigel per injection site) results in rapid tumor growth in intact and castrated hosts on a high cholesterol diet over an 8 week period. Two weeks after tumor cell implantation, the animals are given ezetimibe in their diet at 10 mg/kg body weight. After 6–12 weeks of treatment, examination reveals a marked inhibition of tumor growth and progression compared to untreated controls in both intact and castrated animals.

Example V

SCH 48461 Treatment of SCID Mice Transplanted with LNCaP Cells Transfected with HB-EGF.

In a study similar in design as in example IV animals are given SCH 48461 in their diet at 10 mg/kg body weight.

After 6–12 weeks of treatment examination reveal a significant inhibition of tumor growth and progression as compared to untreated controls in both intact and castrated animals.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described compositions and modes for carrying out the invention which are obvious to those skilled in the art or related fields are intended to be within the scope of the following claims.

What is claimed is:

1. A method of inhibiting the initiation of a cholesterol-associated tumor comprising administering a therapeutically effective amount of an azetidinone-based cholesterol absorption inhibitor to a patient wherein the patient is either at risk of developing a cholesterol-associated tumor or already exhibits a cholesterol-associated tumor wherein the azetidinone-based cholesterol absorption inhibitor is selected from the group consisting of ezetimibe, a glucuronide of ezetimibe, SCH 48461 and SCH 58053.

2. A method according to claim 1 wherein the azetidinone-based cholesterol absorption inhibitor is ezetimibe or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

3. A method according to claim 1 wherein the cholesterol-associated tumor is selected from the group consisting of benign prostatic hypertrophy, benign breast tumor, benign endometrial tumor, and benign colon tumor.

4. A method according to claim 1 wherein the cholesterol-associated tumor is selected from the group consisting of malignant prostate tumor, breast cancer tumor, endometrial cancer tumor, and colon cancer tumor.

5. A method according to claim 1 wherein a therapeutically effective amount is between 0.1 to 30 mg/kg of body weight daily.

6. A method according to claim 2 wherein a therapeutically effective amount is between 0.1 to 30mg/kg of body weight daily.

7. A method of inhibiting the initiation of a cholesterol-associated tumor comprising co-administering a therapeutically effective amount of an azetidinone-based cholesterol absorption inhibitor and at least one other anticancer agent to a patient wherein the patient is either at risk of developing a cholesterol-associated tumor or already exhibits a cholesterol-associated tumor wherein the azetidinone-based cholesterol absorption inhibitor is selected from the group consisting of ezetimibe, a glucuronide of ezetimibe, SCH 48461 and SCH 58053 and at least one other anticancer agent is selected from the group consisting of a steroidal antiandrogen, a non steroidal antiandrogen, an estrogen, diethylstilbestrol, a conjugated estrogen, a selective estrogen receptor modulator (SERM), a taxane, goserelin acetate (ZOLADEX®), and leuprolide acetate (LUPRON®).

8. A method according to claim 7 wherein the azetidinone-based cholesterol absorption inhibitor is ezetimibe.

9. A method according to claim 8 wherein at least one other anticancer agent is selected from the group consisting of a steroidal antiandrogen, a non steroidal antiandrogen, an estrogen, diethyistilbestrol, a conjugated estrogen, a selective estrogen receptor modulator (SERM), a taxane, goserelin acetate (ZOLADEX®), and leuprolide acetate (LUPRON®).

10. A method according to claim 9 wherein the non steroidal antiandrogen is selected from the group consisting of finasteride (PROSCAR®), flutamide (4'-nitro-3'-trifluorormethyl isobutyranilide), bicalutamide (CASODEX®), and nilutamide.

11. A method according to claim 9 wherein the SERM is selected from the group consisting of tamoxifen, raloxifene, droloxifene, and idoxifene.

12. A method according to claim 9 wherein the taxane is selected from the group consisting of paclitaxel (TAXOL®), and docetaxel (TAXOTERE®).

13. A composition for inhibiting the initiation of a cholesterol-associated tumor comprising a therapeutically effective amount of an azetidinone-based cholesterol absorption inhibitor and at least one other anticancer agent wherein the azetidinone-based cholesterol absorption inhibitor is selected from the group consisting of ezetimibe, a glucuronide of ezetimibe, SCH 48461 and SCH 58053 and at least one other anticancer agent is selected from the group consisting of a steroidal antiandrogen, a non steroidal antiandrogen, an estrogen, diethylstilbestrol, a conjugated estrogen, a selective estrogen receptor modulator (SERM), a taxane, goserelin acetate (ZOLADEX®), and leuprolide acetate (LUPRON®).

14. A composition according to claim 13 wherein the azetidinone-based cholesterol absorption inhibitor is ezetimibe and/or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

15. A composition according to claim 14 wherein the non-steroidal antiandrogen is selected from the group consisting of finasteride (PROSCAR®), flutamide (4'-nitro-3'-trifluorormethyl isobutyranilide), bicalutamide (CASODEX®), and nilutamide.

16. A composition according to claim 14 wherein the SERM is selected from the group consisting of tamoxifen, raloxifene, droloxifene, and idoxifene.

17. A composition according to claim 14 wherein the taxane is selected from the group consisting of paclitaxel (TAXOL®), and docetaxel (TAXOTERE®).

18. An article of manufacture comprising a container, instructions, and a composition, wherein the composition comprises a therapeutically effective amount of an azetidinone-based cholesterol absorption inhibitor, and the instructions are for the administration of the composition to inhibit the initiation of a cholesterol-associated tumor or the control of a malignant cholesterol-associated tumor wherein the azetidinone-based cholesterol absorption inhibitor is ezetimibe and/or a stereoisomeric mixture thereof, diastereomerically enriched, diastereomerically pure, enantiomerically enriched or enantiomerically inure isomer thereof, or a prodrug of such compound, mixture or isomer thereof, or a pharmaceutically acceptable salt of the compound, mixture, isomer or prodrug.

19. An article of manufacture according to claim 18 wherein the instructions are for the administration of the composition for a tumor selected from the group consisting of prostatic hypertrophy, breast tumor, endometrial tumor, and colon tumor.

20. An article of manufacture according to claim 18 wherein the composition further comprises at least one other anticancer agent selected from the group consisting of a steroidal antiandrogen, a non-steroidal antiandrogen, an estrogen, diethylstilbestrol, a conjugated estrogen, a selective estrogen receptor modulator (SERM®), a taxane, goserelin acetate (ZOLADEX®), and leuprolide acetate (LUPRON®).

* * * * *

UNITED STATES PATENT AND TRADEMARK OFFICE
CERTIFICATE OF CORRECTION

PATENT NO. : 7,098,198 B2
APPLICATION NO. : 11/128140
DATED : August 29, 2006
INVENTOR(S) : Carl P. Schaffner et al.

It is certified that error appears in the above-identified patent and that said Letters Patent is hereby corrected as shown below:

Title Page Please add Inventor, Item (75): Michael R. Freeman

Col. 1, line 33, after "animals" please add a comma --,--

Col. 3, line 29, please delete "3:57 1-574" and replace with --3:571-574--

Col. 4, line 15, please delete "that" and replace with --those--

Col. 5, line 40, please delete "inhibitors" and replace with --inhibitor--

Col. 8, line 33, please delete "pro static" and replace with --prostatic--

Signed and Sealed this

Fifth Day of August, 2008

JON W. DUDAS
*Director of the United States Patent and Trademark Office*